(12) United States Patent
Patel

(10) Patent No.: US 10,668,019 B2
(45) Date of Patent: Jun. 2, 2020

(54) PROCESS FOR PREPARATION OF A DRUG-POLYMER COMPOSITION

(71) Applicant: Kirit Patel, Ahmedabad (IN)

(72) Inventor: Kirit Patel, Ahmedabad (IN)

( * ) Notice: Subject to any disclaimer, the term of this patent is extended or adjusted under 35 U.S.C. 154(b) by 60 days.

(21) Appl. No.: 15/521,827

(22) PCT Filed: Nov. 26, 2015

(86) PCT No.: PCT/IN2015/050177
§ 371 (c)(1),
(2) Date: Apr. 25, 2017

(87) PCT Pub. No.: WO2016/084105
PCT Pub. Date: Jun. 2, 2016

(65) Prior Publication Data
US 2017/0304205 A1    Oct. 26, 2017

(30) Foreign Application Priority Data

Nov. 30, 2014 (IN) .......................... 2457/MUM/2014

(51) Int. Cl.
*A61K 9/16* (2006.01)
*A61K 9/00* (2006.01)
*A61K 9/28* (2006.01)

(52) U.S. Cl.
CPC .......... *A61K 9/1635* (2013.01); *A61K 9/0056* (2013.01); *A61K 9/1682* (2013.01); *A61K 9/2846* (2013.01)

(58) Field of Classification Search
None
See application file for complete search history.

(56) References Cited

U.S. PATENT DOCUMENTS

| | | | |
|---|---|---|---|
| 5,084,278 A | 1/1992 | Mehta | |
| 5,286,489 A | 2/1994 | Tsau et al. | |
| 6,139,865 A | 10/2000 | Friend et al. | |
| 7,282,218 B2 | 10/2007 | Kulkarni et al. | |
| 7,531,612 B2 | 5/2009 | Kulkarni et al. | |
| 2005/0084540 A1 | 4/2005 | Nandi et al. | |
| 2005/0136115 A1* | 6/2005 | Kulkarni | A61K 9/0095 424/487 |
| 2010/0068252 A1* | 3/2010 | Dias | A61K 9/1635 424/450 |
| 2011/0142942 A1 | 6/2011 | Schobel et al. | |
| 2012/0076858 A1 | 3/2012 | Kolter et al. | |
| 2014/0056981 A1 | 2/2014 | Lopez-Campos et al. | |

FOREIGN PATENT DOCUMENTS

| | | |
|---|---|---|
| EP | 0522141 | 1/1993 |
| EP | 1813268 | 8/2007 |
| EP | 1694724 | 10/2012 |
| EP | 2509631 | 10/2012 |
| WO | WO 92/12704 | 8/1992 |
| WO | WO 2005055986 | 6/2005 |
| WO | WO 2011/072208 | 6/2011 |

OTHER PUBLICATIONS

International Search Report and Written Opinion received in PCT Application No. PCT/IN2015/050177, dated Apr. 25, 2016, 13 pages.

* cited by examiner

*Primary Examiner* — Dominic Lazaro
(74) *Attorney, Agent, or Firm* — Klarquist Sparkman, LLP

(57) ABSTRACT

The present invention relates to an improved active or inactive pharmaceutical ingredient-polymer composition and process of preparation thereof. In particular, the present invention relates to an improved active or inactive pharmaceutical ingredient-polymer composition and process of preparation thereof wherein the monomer encapsulates particles of active or inactive pharmaceutical ingredient at molecular level and with controlled polymerization process the monomer turns into the said polymer coat over the said active or inactive pharmaceutical ingredient that facilitates the disclosed invention to be completed a single step process.

23 Claims, No Drawings

PROCESS FOR PREPARATION OF A DRUG-POLYMER COMPOSITION

CROSS REFERENCE TO RELATED APPLICATIONS

This is the U.S. National Stage of International Application No. PCT/IN2015/050177, filed Nov. 26, 2015, which was published in English under PCT Article 21(2), which in turn claims the benefit of India Application No. 2457/MUM/2014, filed in India on Nov. 30, 2014. Both applications are incorporated herein in their entirety by reference.

FIELD OF INVENTION

The present invention relates to an improved active or inactive pharmaceutical ingredient-polymer composition and process of preparation thereof. In particular, the present invention relates to an improved active or inactive pharmaceutical ingredient-polymer composition and process of preparation thereof wherein the monomer encapsulates particles of active or inactive pharmaceutical ingredient at molecular level and with controlled polymerization process the monomer turns into the said polymer coat over the said active or inactive pharmaceutical ingredient that facilitates the disclosed invention to be completed a single step process.

BACKGROUND AND PRIOR ART

In field of medicament, coating of a polymer barrier is applied to the oral medicament for serving various purposes as below:
Masking taste of bitter molecules;—Sustained release of API;—Enteric coating of API;—Multiple coating;—Film coating;—pH sensitive coating;—Prevent leaching of the coated material into the vehicle;—Stability from the outer atmosphere;—Increase bioavailability of the API;—Stability of light sensitive material;—Stability of moisture sensitive material;—Stability from UV radiation etc.—

Various coating and bitter taste masking techniques are already available in the market but all of them have certain disadvantages as mentioned below:

Complexation Technique

This technique alone is not sufficient enough to taste mask since all complexation techniques have their own limitation in forming a complex and also in release of drug moiety. If a fraction of bitter drug is remained without forming a complex, the end formulation shows bitter taste. Thus further coating with functional polymers is required to attain desired palatability. Moreover, the proper selection of complexing agent is vital as drug release should not be compromised. E.g. cyclodextrins; Proper selection of a cyclodextrin from its available forms is necessary considering drug's lipophilicity and drug molecule size. With excess complexation drug molecules may retain in complexed form and retard the release of drug moiety. Further, the targeted and controlled delivery can't be achieved with this technique.

Ion Exchange Resins Technique

Only ionizable drug reacts with a suitable group of ion exchange resin to form a drug-resinate complex. But it has limited applicability in masking the taste of highly bitter drugs which are not available in ionized form. E.g. Paracetamol, Ornidazole, S-Omeprazole. The selection of ion exchange resin having specific group is difficult as the drug-resinate should be sufficiently stable to prevent its breakdown in salivary fluid and at the same time release the drug completely. Also, this technique has tedious process where to form a complex, drug is to be dispersed in a liquid resin suspension for long duration of time. As the complexion reaction takes place in liquid vehicle only, to formulate a solid dosage it further requires to be dried. Taste masking approach through ion exchange resin makes many compromises in drug delivery. i.e. Complete drug release is not achieved due to retention of drug in complex. Drug-resinate complex releases drug at the stomach pH only, thus delivery at other sites of GI track is not possible. Few drug-resinate complexes are so strong that it delays the release of drug and immediate release is not possible.

Coating Technique

All known coating techniques over the API with different coating materials are described below. Yet all conventional techniques of coating are done with pre synthesized polymers and encapsulation of drug is done in subsequent step. This requires more steps, specialized equipment and skilled person to operate those equipments such ways they are less effective, lengthy and costly process than said invention.

All coating techniques described below requires special coating equipments which require to be handled by the person skilled in the art. Further it requires a carrier vehicle in which coating material is to be solubilized/dispersed. In many cases these vehicle are organic solvents which under process of coating emits into the environment and causes environmental damage. Thus these techniques can't be considered as an eco-friendly process. Over all, with additional step to be performed and using vehicle, these processes become costly.

(i) Lipid and Wax Coating Technique

The taste masking coating using lipids requires that the melting point of the lipid should be sufficiently high to prevent melting in the mouth and should not be as high that active ingredient itself melts or is chemically degraded while processing. Lipid-based microencapsulation requires a highly sophisticated hot melt granulation process for producing fine particles without adversely affecting the drug molecule. Lipid coatings cannot provide masking of bitter taste as efficiently as by coating method using polymers. Moreover, lipid coating results in poor dissolution of the active ingredients in the alimentary track. And it does not provide targeted release of an API.

(ii) Water Soluble Polymer Coating Technique

Use of poly vinyl pyrrolidone, gelatin, methylcellulose, hydroxypropyl methyl cellulose, microcrystalline cellulose and ethyl cellulose are useful in delivering the active ingredients which solubilizes as soon as they come in contact with the aqueous media but such systems cannot be formulated in the liquid dosage forms since there is a possibility of release of the active in the reconstitution media and also the recrystallization of the active ingredient in contact with the aqueous media. Also the Targeted and Controlled delivery can't be achieved with the use of such excipients. Many of the times such coatings fail to mask the bitterness of an API because it solubilises with salaiva fluid.

(iii) Sugar Coating Technique

Use of sugar and other sweeteners for masking the bitter taste of drug is well known, yet complete masking of highly bitter molecules is not possible with this technique. Such systems can't be formulated in the liquid dosage forms since sugar has high water solubility there is a possibility of release of the API in the reconstitution media and also the recrystallization of the active ingredient in contact with the aqueous media. Moreover it acquires long and tedious process which requires specialized equipments and conditions in the formulation. Being a water soluble ingredient targeted and controlled delivery cannot be achieved as is possible with polymers. Sugar coats are tending to show stability problems due to bacterial growth.

(iv) Synthetic Polymer Coating Technique

Conventional polymer coating techniques require pre-synthesized polymer, a vehicle for polymer solution/diapersion, specialized equipment and an operator which overall increases the cost of the product. Further when organic solvent is used as a vehicle, eliminated solvent causes environmental problems. Which do not make these techniques a green process.

Extremely unpleasant tasting active ingredients require a higher concentration of polymer to obtain the desirable level of taste masking. However, this results in delay release of the active ingredient from the formulation. As a result dissolution time is increased and drug does not sufficiently get absorbed. Thus calculated plasma concentration by time is not achieved which further results in poor bioavailability of the said active ingredient.

The conventional coating techniques fail to uniformly coat as using a spray technique there are chances that at certain places the double coat is provided to cover entire surface area which results in uneven coating. And at few places where polymer coat is not covered over the molecules, it results in leaching of drug from those places.

For conventional polymer coating over substances it requires specific equipments such as Coating pan, Auto coater, Fluidized bed coater (top spray and bottom spray), Rapid mixing granulator. All above described equipment's use adds cost to the final product. Furthermore skilled person should be there to operate such specialized equipments. Yet all above described equipments have certain limitations i.e. Coating pan, Auto coater and Fluidized bed coater faces problems of uneven coating, excess coats over the particle, high polymer requirement, lumps formation, flow adjustment of dryer, flow adjustment of spray gun, chocking of the gun, organic solvent loss in the atmosphere etc. Rapid mixing granulator, when used for the purpose of coating, it causes agglomeration of small particles which further requires step of grinding.

As in case of the liquid orals it should be able to keep the drug in a biologically active form. And protect it from contacting with water of the surrounding vehicle, preventing it from converting to other metastable polymorphic forms.

Therefore there is a need for the development of a taste masking drug-polymer composition such that the bitter taste is completely masked by the uniform polymer coat at the pH of saliva in mouth without compromising the drug delivery and also gives promising stability of drug and its formulations.

Conventionally available process for polymer coating over the subject molecules is as described here below:

From this it would be accessed that the said technique is not compatible to address all problems encountered in the said field and it would be appreciated that through a simple technique of manufacturing as in the present case almost all problems are addressed in a neat hand with technical advancement and economically feasible approach.

TABLE 1

| Materials | Processing Steps | | | |
|---|---|---|---|---|
| Step 1: Polymer Synthesis | | | | |
| Vehicle(Organic Solvent) Monomer Catalyst Rehology modifier Inert gas | 1)Polymer Synthesis reaction starting with monomer | 2)Filtration | 3)Drying | 4)Grinding/ Screening |
| Step 2: Polymer coat over Subject Molecule | | | | |
| Vehicle (Aquas/Solvent) Polymer Subject Molecule | 1)Dissolution Of Polymer to make coating material | 2)Coating the subject molecules | 3)Drying | 4)Screening |

Table 1 describes Conventional process with two steps for polymer coating over the subject molecules.

Thus, the conventional process for preparing drug-polymer composition synthesizes a polymer in first step and in subsequent step drug molecule is coated using previously synthesized polymer. Thus, making it two stepped process. Moreover, this process requires comparatively higher amount of pre-synthesized polymer for coating to prepare drug-polymer matrix formation. And using higher amount of pre-synthesized polymer has the disadvantages as mentioned in earlier paragraph.

There are a number of prior art both patented and non-patented literature/documents which use of pre-synthesized polymer as a coating material and coating is done by the process known by the person skilled in the art.

There are various inventions related to coating of drug molecule are published U.S. Pat. No. 7,282,218B2, WO 2005055986A1, U.S. Pat. No. 7,531,612B2 and EP 1694724B1 specifically describe inventions related to coating of drug molecules wherein synthesis of polymer as a prior step and in subsequent step utilizing that polymer, drug molecules are coated with the technique of organic solvent evaporation. Thus, coating is applied using pre-synthesized polymer and with the use of Organic Solvents it adds associated disadvantages. i.e. Loss of organic solvent in the environment, Addition of cost to the process, Handling and storage of organic solvents, Precautions while conducting the process, organic solvents are highly inflammable material, the trace amount in the final drug-polymer composite etc.

U.S. Pat. No. 5,286,489A claims "Porous chewable matrix containing mixture of active drug, flavors, sweeteners and compatible addition homo- or copolymer" wherein this invention discloses preparation of drug-polymer matrix using a pH sensitive polymer which is available in the market under the brand name of Eudragit L 100 and using the said polymer-organic solvent solution the matrix is formed around the active ingredients. Thus, this invention also utilizes pre synthesized polymer.

U.S. Pat. No. 5,084,278A discloses "Taste-masked pharmaceutical compositions" wherein these and other objects are achieved by a pharmaceutical composition comprised of 1) a pharmaceutical core which is further comprised of a pharmaceutically active dose of a compound and, 2) a microencapsulating polymer which coats the pharmaceutical core and is capable of taste-masking the active compound. The said polymers which are indicated in the invention are pre-synthesized and are marketed under the brand name of Eudragit NE30D, Eudragit L30D & Eudragit E30D.

U.S. Pat. No. 6,139,865 claims "Taste-masked microcapsule compositions and methods of manufacture" whereby a composition comprises microcapsules of drug and a substantially water-insoluble polymeric material, typically a cellulosic polymer. But this invention discloses preparation of micro capsule composition using a cellulosic polymer. Thus, in this is also a two step process as pre synthesized polymer is been used. Moreover, polymer of this invention is not able to give pH targeted or sustained release of API due to the use of different nature of polymer.

US 20120076858A1 claims "Orally disintegrating dosage forms containing taste-masked active ingredients" whereby orally disintegrating dosage forms, for the purpose of masking the taste, comprise active ingredients coated with a cationic polymer N,N-diethylaminoethyl methacrylate (DEAEMA). But in this invention in the first stage, polymer is synthesized as dispersion and utilizing that dispersion polymer coat is obtained over the active ingredient in next step. To produce the coating, a copolymer solution in an organic solvent is used. Which adds hazards to the environment. Thus the invention uses pre-synthesized polymer for coating over an ingredient.

US 20050084540 A1 claims "A taste masking composition comprising micropellets containing an antibiotic" wherein said micropellets have an inner coating comprising at least one cellulose polymer which is not an enteric coating polymer and an outer coating comprising an enteric coating polymer, wherein said micropellets have a particle size of about 100 μm to about 650 μm. But this invention discloses a process technique of multiple coat over the antibiotic whereby internal coating is done using cellulose and outer most is enteric coat which is done using pre-synthesized polymer.

EP 0522141A1 claims "Method for masking the taste of a medicament" wherein taste-masking composition for oral delivery of medicaments to non-ruminants, especially humans is disclosed. But this invention discloses composition comprising medicament and its coating using combination of coating materials, waxes and pre-synthesized polymers.

EP 2509631A1 discloses "pH sensitive compounds in taste masking within oral thin film strips. However, it discloses a multiple coat over the active ingredient granules. Inner coat is a moisture barrier coat, and outer coat is a film coat which provides the taste masking of the formulation whereby the polymers used are pre-synthesized.

Thus, all available prior art in the said technical field discloses synthesis of polymers in first step and in subsequent step using previously synthesized polymer, drug molecule is been coated. Most of them are using solvent as a polymer vehicle which emits in to the environment during the process. Thus all available prior arts are two stepped process and the disadvantages/shortcomings of the two step process has already been discussed in the above paragraphs and the typical disadvantages are also discussed below under the headings "DISADVANTAGES OF PRIOR ART". Moreover, comparatively higher amount of pre-synthesized polymer is required for preparing drug-polymer matrix formation. Also there are high chances that use of the higher amount of pre-synthesized polymer for complete taste mask of drug may not fall within the permissible limits of the polymer amount described in standards.

DISADVANTAGES OF PRIOR ART

All of the existing prior art techniques for coating drug molecules suffer from at least one of the below mentioned disadvantages:

Many of them cannot fully mask the taste of highly bitter drugs;

In all of the existing techniques polymers are synthesized in first step and in subsequent step (Active Pharmaceutical Ingredient) API is coated using previously synthesized polymer, thus making it two step process;

In many cases vehicle is an Organic Solvent, which under process of coating emits into the environment and causes environmental damage and also increases the cost of process.

All of them require significantly higher amount of polymer to encapsulate extremely unpleasant tasting drug molecule resulting in cost addition of the process;

Use of higher amount of polymer to encapsulate extremely unpleasant tasting drug molecule results in delayed release of the active ingredient from the formulation which further results in poor bioavailability of the API;

None of them can be used for all class of drugs. e.g. complexation;

None of them can be used for all type of dosage form such as liquid dosage form cannot be coated by water soluble polymers i.e. PVP;

Most of them fail to form a uniform coat over the particles which result in leaching of drug and also affects the stability of the compound;

Non-uniform coating causes stability issues to the particles which were intended to get protected from the unfavorable surroundings.

Many of them do not provide targeted or controlled delivery of the API;

Some of them are not able to be formulated in the liquid dosage forms since there is a possibility of release of the API in the reconstitution media and also the re-crystallization of the active ingredient in contact with the aqueous media;

Many of them do not allow drugs to get sufficiently absorbed and so patient does not get effective therapeutic concentration in the plasma such as in Ion exchange resin technique;

All of them are higher in cost due to more number of steps involved in the process where all of them uses pre synthesized polymers;

Most of them have comparatively poor bioavailability;

Many of them face the problem of drug leaching;

Many of them require specialized men power, equipments and conditions in the formulation which at the end increases the cost of the overall process.

Thus, there is a need to come up with an invention which overcomes the problems of prior art.

Objects of the Invention

The main object of the invention is to provide improved drug-polymer composition and process of preparation thereof whereby monomer encapsulates particles of active or inactive ingredient at molecular level and with controlled polymerization process monomer turns into polymer covering the said active or inactive ingredient which makes the proposed invention a single step coating process.

Another object of invention is to provide improved drug-polymer composition and process of preparation thereof which is an organic solvent free, eco friendly and cost-effective process which uses water as a preferable vehicle.

Another object of the invention is to provide improved drug-polymer composition and process of preparation thereof using single step process which starts with monomer and ends with uniform polymer coat over active-inactive ingredient.

Another object of invention is to provide improved drug-polymer composition and process of preparation thereof which facilitates uniform and thin polymer coating utilizing significantly less amount of polymer which immediately releases the drug molecules at the site of delivery resulting in the improved bioavailability of drug molecule.

Yet another object of invention is to provide improved drug-polymer composition and process of preparation thereof which facilitates uniform coating which prevents conversion of active pharmaceutical ingredient from its stable form to metastable form which in turn increases stability of the drug and shelf life of the product composite.

Further object of the invention is to provide improved drug-polymer composition and process of preparation thereof which provides immediate drug release at required targeted pH.

Further object of the invention is to provide improved drug-polymer composition and process of preparation thereof which is cost- effective.

Further object of the invention is to provide improved drug-polymer composition and process of preparation thereof which involves less process step, recourses and men power.

Further object of the invention is to provide improved drug-polymer composition and process of preparation thereof which provides covering of monomer/s over the individual active or inactive ingredient particle's surfaces, giving better and thinner polymer coating.

Further object of the invention is to provide improved drug-polymer composition and process of preparation thereof which can be used to coat all class of drugs, amorphous, crystalline, salt form of drug, drug complexes, pro drugs, co-crystal, solvate form of drug, hydrate form of drug and all polymorphic form of the drug.

Further object of the invention is to provide improved drug-polymer composition and process of preparation thereof which can coat over any size of subject particles.

Further object of the invention is to provide improved drug-polymer composition and process of preparation thereof which can be incorporated in wide range of formulations such as solid, liquid, semisolid and all possible dosage forms.

Further object of the invention is to provide process of preparation for improved drug-polymer composition for all of the products as discussed above:

Further object of the invention is to provide improved drug-polymer composition and process of preparation thereof which allow drugs to get sufficiently absorbed and facilitating effective therapeutic concentration of the drug in the plasma.

Further object of the invention is to provide improved drug-polymer composition and process of preparation thereof which is efficiently able to mask the taste of extremely bitter taste drugs with significantly less amount of polymer.

Further object of the invention is to provide improved drug-polymer composition and process of preparation thereof which prevents the problem of drug leaching.

Further object of the invention is to provide improved drug-polymer composition and process of preparation thereof which coat the drug molecules which are Light/UV sensitive.

Further object of the invention is to provide improved drug-polymer composition and process of preparation thereof which coat the drug molecules which are Moisture sensitive.

Further, object of the invention is to provide improved drug-polymer composition and process of preparation thereof which is able to coat over material with all possible particle sizes and with all possible physical forms i.e. organic/inorganic, water soluble/insoluble.

DESCRIPTION OF INVENTION

The main embodiment of the invention is to provide improved drug-polymer composition and process of preparation thereof using single step coating process. A single step process which start with monomer and ends with uniform polymer coat over active-inactive ingredients.

The proposed improved drug-polymer composition prepared using single step coating process mainly comprises of:
Active/inactive Pharmaceutical ingredient;
Vehicle;
Monomer/s
Catalyst
Excipients.

The proposed improved drug-polymer composition is prepared using single step coating process as below:

Fine particles of active ingredient of drug and monomer are dispersed in the vehicle solution where monomer/s layer uniformly covers the individual particles of active ingredient of drug and the polymerization process is carried out for formation of polymer from monomer which simultaneously entrap particles of Active/inactive Pharmaceutical ingredient into polymer shell at molecular level making the proposed invention, a single step coating process.

Table 2 describes Proposed invention with single step for polymer coat over subject molecules.

The proposed improved drug-polymer composition comprising of:
(a) Preparing a uniform blend of the vehicle (water) saturated with salt and surfactants as part A;
(b) Preparing a blend of the desired amount of active drug and thickener and adding it to part A with constant stirring keeping the suspension over a desired period of time in

TABLE 2

❖ Proposed Single step Polymer coat over the Subject molecules

| Materials | Processing Steps | | | |
|---|---|---|---|---|
| Vehicle (Water) | 1)Reaction | 2)Filtration | 3)Drying | 4)Screening |
| Monomer | Starting with | | | |
| Subject Molecule | monmer and | | | |
| Catalyst | subject | | | |
| Rehology modifier | molecule | | | |
| Inert gas | | | | | desired temperature as part B;
(c) preparing a catalyst content with desired amount of DM water as part C;

(d) Adding part C to part B with constant stirring and maintaining the desired temperature as part D;
(e) Separately preparing a homogeneously blend containing desired monomers, from which polymer is formed, and a catalyst and pouring the entire content to the uniformly dispersed part D;
(f) Initiating the reaction in an inert atmosphere for complete polymerization of the monomer, over the subject molecules, in the contents of step (e) by maintaining the desired pH, temperature, pressure and time;
(g) Recovering the polymerized product by filtration and washing repeatedly;
(h) Feeding the contents of step (g) to a spray drier for drying the final product.

The said monomers are chosen as per the required property of final drug-polymer composition and as per the required function of the polymer coat.

The said monomer is a derivative of acrylic acid and methacrylic acid.

Referring to Acrylic Acid derivatives are selected from the group consisting of:

Acrylic acid, Bromo acrylic acid, Bromo methyl acrylic acid, Ethylacrylic acid, Carboxyethyl acrylate, Propylacrylic acid, Fluoromethylacrylic acid, Benzoylhydroxyphenoxyethyl acrylate, Benzylpropylacrylate, Butyl acrylate, Butyl aminocarbonyl oxyethyl acrylate, Butyl bromoacrylate, Butylcyclohexyl acrylate, Carboxyethyl acrylate, Chloroethyl acrylate, Diethylamino ethyl acrylate, Ethylene glycol ethyl ether acrylate, Ethylene glycol ethylhexyl ether acrylate, Dimethylamino ethyl acrylate, Dimethylamino propyl acrylate, Ethyl acrylate, Bromomethyl acrylate, Cyano acrylate, Ethylene glycol dicyclopentenyl ether acrylate, Ethylene glycol methyl ether acrylate, Ethylene glycol phenyl ether acrylate, Ethyl ethylacrylate, Ethyl hexyl acrylate, Ethyl propylacrylate, Ethyl trimethylsilylmethyl acrylate, Hexyl acrylate, Hydroxybutyl acrylate, Hydroxyethyl acrylate, Hydroxy phenoxypropyl acrylate, Hydroxypropyl acrylate, Bornyl acrylate, Butyl acrylate, Decyl acrylate, Octyl acrylate, Lauryl acrylate, Methacrylic acid, Methyl acetamidoacrylate, Methyl acrylate, Methyl bromoacrylate, Methyl bromomethylacrylate, Methyl chloromethyl acrylate, Methyl hydroxy methylenebutyrate, Methyl fluoromethyl acrylate, Octadecyl acrylate, Pentabromobenzyl acrylate, Pentabromophenyl acrylate, Pentafluorophenyl acrylate, Polyethyleneglycol acrylate, Polyethyleneglycol diacrylate, Polyethyleneglycol methyl ether acrylate, Polypropyleneglycol acrylate, Tetrahydrofurfuryl acrylate, Tetrahydropyranyl acrylate, Trimethoxysilyl propyl acrylate, Trimethylhexyl acrylate, Undecenyl acrylate Referring to Methacrylic acid derivatives are selected from the group consisting of:

Allyl methacrylate, Aminoethyl methacrylate hydrochloride, Benzotriazol hydroxyphenyl ethy methacrylate, Benzyl methacrylate, Amino ethyl methacrylate, Bromoisobutyryloxy ethyl methacrylate, Butylamino ethyl methacrylate, Butyl methacrylate, Carbazole ethylmethacrylate, Chloro hydroxypropyl methacrylate, Cyclohexyl methacrylate, Diethylamino ethyl methacrylate, Diethylene glycol butyl ether methacrylate, Diethylene glycol methyl ether methacrylate pricing, Diisopropylamino ethyl methacrylate, Dimethylamino ethyl methacrylate, Ethoxyethyl methacrylate, Ethyleneglycol dicyclopentenyl ether methacrylate, Ethyleneglycol methacrylate phosphate, Ethyleneglycol methyl ether methacrylate, Ethyleneglycol phenyl ether methacrylate, Ethylhexyl methacrylate, Ethyl methacrylate, Ferrocenylmethyl methacrylate, Furfuryl methacrylate, Glycidyl methacrylate, Glycidyl methacrylate, Glycosyloxyethyl methacrylate, Hexyl methacrylate, Hydroxybutyl methacrylate, Hydroxyethyl methacrylate, Hydroxypropyl methacrylate, Bornyl methacrylate, Isobutyl methacrylate, Isocyanatoethyl methacrylate, Isodecyl methacrylate, Lauryl methacrylate, Methyl methacrylate, methylthioethyl methacrylate, Methacryloyloxyethyl maleate, Methacryloyloxyethyl succinate, Morpholinoethyl methacrylate, Naphthyl methacrylate, Imidazolidinyl ethyl methacrylate, Pentabromophenyl methacrylate, Pentafluorophenyl methacrylate, Phenylene dimethacrylate, Phenyl methacrylate, Polyethylene glycol behenyl ether methacrylate, Polypropylene glycol methacrylate, Propyl methacrylate, Pyrenemethyl methacrylate, Solketal methacrylate, Stearyl methacrylate, TEMPO methacrylate, Tetrahydrofurfuryl methacrylate, Tribromophenyl methacrylate, Trichlorosilyl propyl methacrylate, Triethylene glycol methyl ether methacrylate, Trimethoxysilyl propyl methacrylate, Trimethylcyclohexyl methacrylate, Trimethylsilyl methacrylate, Trimethylsilyloxy ethyl methacrylate, Trimethylsiloxy silyl propyl methacrylate, Vinyl methacrylate.

Moreover, said vehicle, monomer/s and subject particles are either miscible/immiscible and soluble/insoluble with each other.

The said excipients as proposed in the instant invention are plasticizer, coloring agent or any property modifier etc.

In the proposed invention, the preferred polymerization catalysts suitably are redox initiators. Photo initiator can also be used.

Referring to the redox initiators any of the well known water soluble reducing agents and oxidizing agents can be used. Examples of reducing agents include such as ascorbic acid, alkali metal sulfites, alkali metal bisulfates, ammonium sulfite, ammonium bisulfate, alkali metal hydrogen sulfite, ammonium hydrogen sulfite, ferrous metal salts i.e ferrous sulfates.

Referring to Oxidizing agents include compounds such as hydrogen peroxide, benzoyl peroxide alkali metal persulfate, ammonium persulfate, alkyl hydro peroxides, peresters, diacyl peroxides, silver salts etc.

Preferable redox initiators and oxidizing agents are redox initiator Azobisisobutyronitrile (aibn), Sodium persulfate, Potassium persulfate, benzoyl peroxide.

Referring to rheology modifier which are used as viscosity enhancing agent and wetting agent A viscosity enhancer is selected from the group consisting of acacia, carbomer, carboxy methyl cellulose calcium, carboxy methyl cellulose sodium, hydroxy ethyl cellulose hydroxy propyl cellulose, hydroxy propyl methyl cellulose, methylcellulose, polyvinyl pyrrolidone, powdered cellulose, sodium alginate and tragacanth, guar gum, gum acacia, xenthan gum.

A wetting agent is selected from Surfactant groups of Ionic surfactants, Anionic surfactants, Non ionic surfactants and Amphoteric surfactants.

The said process is carried out at a temperature in the range of 20-95° C. and for a period of 1-24 hours. The polymerization of monomer over the subject molecule is carried out for 1 to 2 hours.

Drying of synthesized drug-polymer composite is carried out by any means of drying techniques i.e. Spray dryer, Spinn flash dryer, fluidized bed drier, ect. The drying is carried out at the temperature range of 40 to 200° C. The drying is carried out at lower temperature with vacuum for temperature sensitive subject molecules where the properties of subject molecules are unaffected throughout the drying process is carried out.

In the proposed invention, the active ingredient of drug having possible small particle size is dispersed in a vehicle without agglomeration and a monomeric layer is formed on/at the surface of individual active ingredient particles. Thus, the close and uniform contact of monomer over the active/inactive ingredient particles is maintained while it transits from monomer to polymer. The better layer of monomer/s into subject molecule's surfaces gives uniform, smooth and thinner polymer coating.

Moreover, said drug-polymer composite is synthesized from 0.1 micron to 900 microns particle size. And required thickness of polymer coat is obtained as only predetermined monomer turns into polymer (with desired molecular weight) and no excess polymeric material remains into the vehicle solution. The percentage of polymer used in the proposed invention for matrix formation falls under limits as per the pharmacopeia standards.

In the proposed invention, due to the less amount of the polymer used, drug to polymer ratio is high which reduces the size of the dose.

The proposed process is used to coat all class of drugs, amorphous, crystalline, salt form of drug, drug complexes, pro drugs, co-crystal, solvate form of drug, hydrate form of drug and all polymorphic form of the drug.

Further, the proposed invention is able to coat over material with all possible particle sizes and all possible physical forms organic/inorganic and water soluble/insoluble.

The proposed process of preparation for improved drug-polymer composition is provided for all of the below mentioned purposes:

Taste masking of bitter molecules;—Sustained release of API

Enteric coating; -Multiple coating;—Film coating;

pH sensitive coating;

Prevent leaching of the coated material into the vehicle

Stability from the outer atmosphere;—Increase bioavailability of the API

Stability of light sensitive material;—Stability from UV radiation etc.

Stability of moisture sensitive material

The proposed invention provides improved bioavailability of drug molecule by (i) Providing fine drug-polymer composition which facilitates larger surface area which further increases the rate of dissolution resulting in the improved bioavailability of drug molecule and (ii) Providing uniform coating which immediately releases the drug molecules at the site of delivery resulting in the improved bioavailability of drug molecule.

(iii) Release of a drug at specific pH site where drug has highest solubility, increasing the bioavailability.

Moreover, the proposed invention provides uniform thickness and smooth surface throughout the drug polymer composition. Further, as the entire individual active ingredient particles are covered, the problems of drug leaching out as well as vehicle penetration are prevented. This makes the drug molecules intact from the surroundings. Thus, suspension/dry syrup or any formulation where vehicle causes problem in drug stability are prevented from the proposed process and all API can be formulated in liquid dosage form.

Further, the proposed invention is able to coat, the fine small particles of API having large surface area, with the polymer having solubility at specific pH. So synthesized polymer over the API gives immediate drug release at the desired pH of the site. Polymer can be synthesized with the choice of monomers depending on the required final property of the pH sensitive polymer. Proposed invention can synthesis polymer-drug composition which can successfully deliver the API at site of actions such as oral, nasal, vaginal and rectal. Thus, the proposed invention is provided to facilitate drug delivery at wide ranges of pH.

Further, the proposed invention also provides modified to drug delivery system whereby outer most coat is of pH sensitive polymer (Targeted release) and inner coat releases the drug at slow rate at the site of delivery (Sustained release).

Also, the proposed invention is used to coat the drug molecules are tending to turn in to crystalline form in contact with water, preventing them to turn to metastable forms preventing the problems of poor solubility and low dissolution rate. Moreover, the proposed invention is also used to coat drug molecules which are Light/UV sensitive.

The proposed improved drug-polymer composition and process of preparation thereof facilitates uniform coating which keeps active pharmaceutical ingredient intact in the polymer coat which in turn increases stability of the drug and shelf life of the product composite.

Another embodiment of the invention is to provide heat sensitive vitamin coat, coating of metal molecules which tend to oxidize, enzyme coat for its stability and encapsulation of neutraceutical products and coloring agent.

After discussing the invention on its practical aspect of its operation and the result it is suppose to deliver, it becomes warranted to see its feasibility in working capacity through examples. This indeed ascertains whether the objective as proposed in the invention, would be realized or not.

The following parameters are used for descriptive purposes as well as the intended use of the following materials for the experimental purposes without any limiting terms.

TM: Taste Masking; SR: Sustained Release; CT: Colon Targeted; BP: Bacterial protection;

SM: Smell Masking; EC: Enteric Coat; MF: Moisture protective Film; OF: Oxidation protective Film etc.

Monomers used throughout the invention are MM—Methylmethacrylate; MAA—Methyl Acrylic Acid; EA—Ethyl Acrylate; MA—Methyl Acrylae; BA—Butyl Acrylate; DMA—Dimethylacrylamide and; BM—Butyl Methacrylate wherein the molecular weight of the polymer formed out of the monomer ranges from 10,000 to 7,00,000.

Surfactants are of the following category as S3: SLS (Sodium Lauryl Sulphate); S4: SLES(Sodium Lauryl Ethyl Sulphate); T3: Tween 60; T4: Tween 80; L 1: Lecithin; E 1: Castor Ethoxylate; E2: Soya Ethoxylate; S1: Soritan Mono Oleate; S2: Sorbitn Mono Stearate etc.

Catalyst are as depicted, CAT A—azo iso bis nitoryl (aibn), CAT-N Sodium persulfate, CAT P—Potassium persulfate, CAT G—benzoyl peroxide.

Thickeners are SC: Sodium CMC; XG: Xenthan Gum; GG: Guar Gum etc. and

Salts used throughout the experiments are classified under the nomenclature are: Yes- Added, where subject molecule is Water soluble/Partially water soluble; and No-Not added, where subject molecule is Water insoluble.

(I) Azithromycin Dihydrate, Paracetamol, Cephalexin, Chloroquine, Erythromycin, Linezolid are Intended to Prepare Sustained Release (SR) Polymer Coat Over the Subject Molecules Example 1: Azithromysin-Polymer Composition is Intended to Prepare Sustained Release (SR) Coat Over the Subject Molecules PART A: 150 ml of Water is taken as a Vehicle. Furthermore, viscosity of vehicle is increased with the aid of Viscosity enhancer such as 1 gm Sodium CMC, and water miscible surfactant 1 gm of Lecithin is mixed properly to form a uniform blend.

PART B: Subject Molecule 32.5 gm Azithromycin is slowly added into PART A with constant stirring and the suspension is kept under stirring for 30 minutes.

PART C: The Monomers (DMA 8.75 gm, MM 4.38 gm, and BM 4.38 gm) were mixed in separate container for 10 minutes. After that a Catalyst "Cat A" 1.2 gm is mixed to the homogeneously blended monomers.

PART C is poured into uniform dispersion of PART B and Part A as above:

For reaction to initiate and complete the drug and monomer mixture is kept at 55-75° C. & pressure 2 kg for Time 6 hrs.

pH of the reaction was maintained at 8.5-9.

The reaction mixture was purged with the nitrogen to provide an inert atmosphere.

The polymer coated over Azithrmycin micro particles so synthesized was recovered by filtration and given few washes of water. Once washing is done it is redispersed in water to make a feed of spray dryer, and so dried uniform powder is collected out of the spray dryer.

Example 2: Paracetamol-Polymer Composition is Intended to Prepare Sustained Release (SR) Coat Over the Subject Molecules as Per the Scheme of Example 1

PART A: 300 ml Water is taken as a vehicle and is saturated with 100 gm Salt. Furthermore, viscosity of vehicle is increase with the aid of viscosity enhancer, 2 gm Sodium CMC and water miscible surfactant 1 gm Soya ethoxylate is mixed proper to form a uniform blend.

PART B: Subject Molecule 50 gm Paracetamol is slowly added into PART A with constant stirring and the suspension is kept under stirring for 30 minutes.

PART C: The monomers (DMA 25 gm, MM12.5 gm, and BM 12.5 gm) were mixed in separate container for 10 minutes. After that Catalyst "Cat A" 3.5 gm and "Cat N" 0.2 gm are mixed to the homogeneously blended monomers.

PART C is poured into uniform dispersion of PART B and PART A

For reaction to initiate and complete the drug and monomer mixture is kept at 60-75° C. & Pressure 2 kg for time 5 hrs.

pH of the reaction was maintained at 7-8.

And the reaction mixture was purged with the nitrogen gas to provide the inert atmosphere.

The polymer coated over Paracetamol micro particles so synthesized was recovered by filtration and given few washes of water. Once washing is done it is redispersed in water to make a feed of spray dryer, and so dried uniform powder is collected out of the spray dryer.

Example 3: Cephalexin-Polymer Composition is Intended to Prepare Sustained Release (SR) Coat Over the Subject Molecules PART A: 350 ml Water is taken as a vehicle and is saturated with 110 gm Salt. Furthermore, viscosity of vehicle is increase with the aid of viscosity enhancer 1 gm Xethan gum. And water miscible surfactant 1 gm Tween80 and 0.4 gm SLES is mixed proper to form a uniform blend.

PART B: Subject molecule 50 gm Cephalexin is slowly added into PART A with constant stirring and the suspension is kept under stirring for 30 minutes.

PART C: The monomers (DMA 15 gm, MM 17.5 gm, and BM 17.5 gm) were mixed in separate container for 10 minutes. After that Catalyst "Cat A" 3 gm is mixed to the homogeneously blended monomers.

PART C is poured into uniform dispersion of PART B and PART A

For reaction to initiate and complete the drug+monomer mixture is kept at 75-80° C. & Pressure 1 kg for 5 hrs-30 minutes.

pH of the reaction was maintained at 3-6.

And the reaction mixture was purged with the nitrogen gas to provide the inert atmosphere.

The polymer coated over Cephalexin micro particles so synthesized was recovered by filtration and given few washes of water. Once washing is done it is redispersed in water to make a feed of spray dryer, and so dried uniform powder is collected out of the spray dryer.

Example 4: Chloroquine Phosphate-Polymer Composition is Intended to Prepare Sustained Release (SR) Coat Over the Subject Molecules PART A: 350 ml water is taken as a vehicle and is saturated with 110 gm Salt. Furthermore, viscosity of vehicle is increase with the aid of viscosity enhancer 1 gm Xethan gum and water miscible surfactant 1 gm Tween80 and 0.4 gm SLES is mixed proper to form a uniform blend.

PART B: Subject molecule 50 gm Chloroquine Phosphate is slowly added into PART A with constant stirring and the suspension is kept under stirring for 30 minutes.

PART C: The monomers (DMA 15 gm, MM 17.5 gm, and BM 17.5 gm) were mixed in separate container for 10 minutes. After that catalyst "Cat A" 3 gm is mixed to the homogeneously blended monomers.

PART C is poured into uniform dispersion of PART B and PART A

For reaction to initiate and complete the drug and monomer mixture is kept at 80-85° C. & pressure 2 kg for time 5 hr.

pH of the reaction was maintained at 4-6.5.

And the reaction mixture was purged with the nitrogen gas to provide the inert atmosphere.

The polymer coated over Chloroquine Phosphate micro particles so synthesized was recovered by filtration and given few washes of water. Once washing is done it is redispersed in water to make a feed of spray dryer, and so dried uniform powder is collected out of the spray dryer.

Example 5: Erythromycin Ethyl Sucsinate-Polymer Composition is Intended to Prepare Sustained Release (SR) Coat Over the Subject Molecules PART A: 250 ml water is taken as a vehicle and is saturated with 65 gm salt. Furthermore, viscosity of vehicle is increased with the aid of viscosity enhancer 1 gm Guar gum and water miscible surfactant 1 gm SLS is mixed proper to form a uniform blend.

PART B: Subject molecule 50 gm Erythromycin Ethyl Succinate is slowly added into PART A with constant stirring and the suspension is kept under stirring for 30 minutes.

PART C: The monomers (DMA 25 gm, MM 12.5 gm, and MA 12.5 gm) were mixed in separate container for 10 minutes. After that catalyst "Cat A" 0.4 gm and "Cat P" 1 gm are mixed to the homogeneously blended monomers.

PART C is poured into uniform dispersion of PART B and PART A

For reaction to initiate and complete the drug and monomer mixture is kept at 75-80° C. & Pressure 1.5 kg for time 5 hr.

pH of the reaction was maintained at 8.5-9.

And the reaction mixture was purged with the nitrogen gas to provide the inert atmosphere.

The polymer coated over Erythromycin Ethyl Succinate micro particles so synthesized was recovered by filtration and given few washes of water. Once washing is done it is redispersed in water to make a feed of spray dryer, and so dried uniform powder is collected out of the spray dryer.

Example 6: Linezolid-Polymer Composition is Intended to Prepare Sustained Release (SR) Coat Over the Subject Molecules PART A: 400 ml Water is taken as a vehicle and is saturated with 130 gm salt. Furthermore, viscosity of vehicle is increase with the aid of viscosity enhancer 1 gm Sodium CMC and water miscible surfactant 1 gm Castor Ethoxlate is mixed proper to form a uniform blend.

PART B: Subject molecule 50 gm Linezolid is slowly added into PART A with constant stirring and the suspension is kept under stirring for 30 minutes.

PART C: The monomers (DMA 25 gm, MM 12.5 gm, and MA 12.5 gm) were mixed in separate container for 10 minutes. After that catalyst "Cat A" 2 gm is mixed to the homogeneously blended monomers.

PART C is poured into uniform dispersion of PART B and PART A

For reaction to initiate and complete the drug and monomer mixture is kept at 70-85° C. & pressure 2 kg for time 5 hr.

pH of the reaction was maintained at 8.5-9.

And the reaction mixture was purged with the nitrogen gas to provide the inert atmosphere.

The polymer coated over Linezolid micro particles so synthesized was recovered by filtration and given few washes of water. Once washing is done it is redispersed in water to make a feed of spray dryer, and so dried uniform powder is collected out of the spray dryer.

(II) Clarithromysin and Ampicilin are Intended to Prepare Colone Targeted (CT) Release Polymer Coat Over the Subject Molecules Example 7: Clarithromycin-Polymer Composition is Intended to Prepare Colone Targeted (CT) Coat Over the Subject Molecules PART A: 200 ml water is taken as a vehicle. Furthermore, viscosity of vehicle is increase with the aid of viscosity enhancer 1 gm Sodium CMC and water miscible surfactant 0.4 gm Lecithin is mixed proper to form a uniform blend.

PART B: Subject molecule 25 gm Clarithromycin is slowly added into PART A with constant stirring and the suspension is kept under stirring for 30 minutes.

PART C: The monomers (DMA 13 gm, MM 6 gm, and BM 6 gm) were mixed in separate container for 10 minutes. After that catalyst "Cat A" 2 gm is mixed to the homogeneously blended monomers.

PART C is poured into uniform dispersion of PART B and PART A

For reaction to initiate and complete the drug and monomer mixture is kept at 55-75° C. & pressure 1 kg for time 6 hr.

pH of the reaction was maintained at 8.5-9.

And the reaction mixture was purged with the nitrogen gas to provide the inert atmosphere.

The polymer coated over Clarithromycin micro particles so synthesized was recovered by filtration and given few washes of water. Once washing is done it is redispersed in water to make a feed of spray dryer, and so dried uniform powder is collected out of the spray dryer.

Example 8: Ampicillin-Polymer Composition is Intended to Prepare Colone Targeted (CT) Coat Over the Subject Molecules PART A: 300 ml water is taken as a vehicle. Furthermore, viscosity of vehicle is increase with the aid of viscosity enhancer 1 gm Sodium CMC and water miscible surfactant 1 gm Castor Ethoxylate is mixed proper to form a uniform blend.

PART B: Subject molecule 50 gm Ampicillin is slowly added into PART A with constant stirring and the suspension is kept under stirring for 30 minutes.

PART C: The monomers (DMA 20 gm, MM 15 gm, and BM 15 gm) were mixed in separate container for 10 minutes. After that catalyst "Cat A" 4 gm is mixed to the homogeneously blended monomers.

PART C is poured into uniform dispersion of PART B and A

For reaction to initiate and complete the drug and monomer mixture is kept at 80-85° C. & pressure 1.5 kg for time 5 hr.

pH of the reaction was maintained at 5-7.5.

And the reaction mixture was purged with the nitrogen gas to provide the inert atmosphere.

The polymer coated over Ampicillin micro particles so synthesized was recovered by filtration and given few washes of water. Once washing is done it is redispersed in water to make a feed of spray dryer, and so dried uniform powder is collected out of the spray dryer.

(III) Metronidaole, Ibuprofen and Cefadroxyl are Subjected for the Enteric Coat (EC) which are Released at the pH of Stomach Example 9: Metronidazole Benzoate-Polymer Composition is Intended to Prepare Enteric Coat (EC) Over the Subject Molecules PART A: 400 ml water is taken as a vehicle. Furthermore, viscosity of vehicle is increased with the aid of viscosity enhancer 2 gm Sodium CMC and water miscible surfactant 1 gm Soya Ethoxylate are mixed proper to form a uniform blend.

PART B: Subject molecule 50 gm Metronidazole Benzoate is slowly added into PART A with constant stirring and the suspension is kept under stirring for 30 minutes with heating temperature at 78° C.

PART C: A catalyst "Cat G" 0.5 gm with DM water is prepared in different container.

Once temperature is gained PART C is poured to above suspension mixture (A+B) with constant stirring.

PART D: Monomer (AA 25 gm, MA 25 gm) were used for the synthesis of the polymer. The monomers were mixed in separate container. A catalyst "Cat A" 0.5 gm is mixed with the monomer blend homogeneously.

PART D is poured into uniform dispersion prepared above PART (A+B+C)

For reaction to initiate and complete the polymerization of monomer over the subject molecule, the mixture is kept at 78-80° C. and pressure 2 kgs for time 6 hrs. pH of the reaction was maintained at 5-7.

And the reaction mixture was purged with the nitrogen gas to provide the inert atmosphere.

The polymer coated Lactic Acid micro particles so synthesized was recovered by filtration and given few washes of water. Once washing is done it is re dispersed in water to make a feed of spray dryer.

Example 10: Ibuprofen-Polymer Composition is Intended to Prepare Enteric Coat (EC) Over the Subject Molecules PART A: 200 ml water is taken as a vehicle and saturated with 65 gm salt. Furthermore viscosity of vehicle is increased with the aid of viscosity enhancer 1 gm Sodium CMC. And water miscible surfactant 1 gm Lecithin are mixed proper to form a uniform blend.

PART B: Subject molecule 35 gm Ibuprofen is slowly added into PART A with constant stirring and the suspension is kept under stirring for 30 minutes with heating temperature at 60° C.

PART C: A catalyst "Cat N" 0.11 gm with DM water is prepared in different container.

Once temperature is gained PART C is poured to above suspension mixture (A+B) with constant stirring.

PART D: Monomer (MAA 7.5 gm, EA 7.5 gm) were used for the synthesis of the polymer. The monomers were mixed in separate container. A catalyst "Cat A" 0.38 gm is mixed with the monomer blend homogeneously.

PART D is poured into uniform dispersion prepared above to PART (A+B+C).

For reaction to initiate and complete the polymerization of monomer over the subject molecule, the mixture is kept at 60-75° C. and pressure 1 kgs for time 6 hrs. pH of the reaction was maintained at 2.5-3.

And the reaction mixture was purged with the nitrogen gas to provide the inert atmosphere.

The polymer coated Lactic Acid micro particles so synthesized was recovered by filtration and given few washes of water. Once washing is done it is re dispersed in water to make a feed of spray dryer.

Example 11: Cefadroxil-Polymer Composition is Intended to Prepare Enteric Coat (EC) Over the Subject Molecules PART A: 400 ml water is taken as a vehicle and saturated with 120 gm salt. Furthermore, viscosity of vehicle is increase with the aid of viscosity enhancer 1 gm HPMC. And water miscible surfactant 0.6 gm SLS and 0.8 gm Tween60 are mixed proper to form a uniform blend.

PART B: Subject molecule 50 gm Cefadroxil is slowly added into PART A with constant stirring and the suspension is kept under stirring for 30 minutes with heating temperature at 75° C.

PART C: A catalyst "Cat N" 0.8 gm with DM water is prepared in different container.

Once temperature is gained PART C is poured to above suspension mixture PART (A+B) with constant stirring.

PART D: Monomer (MAA 5 gm, MM 13.5 gm, MA 31.5 gm) were used for the synthesis of the polymer. The monomers were mixed in separate container.

PART D is poured into uniform dispersion prepared above PART (A+B+C)

For reaction to initiate and complete the polymerization of monomer over the subject molecule, the mixture is kept at 75-80° C. and pressure 1 kgs for time 6 hr. pH of the reaction was maintained at 2.5-3.

And the reaction mixture was purged with the nitrogen gas to provide the inert atmosphere.

The polymer coated Lactic Acid micro particles so synthesized was recovered by filtration and given few washes of water. Once washing is done it is re dispersed in water to make a feed of spray dryer.

(IV) Lactic Acid is Intended to the Bacterial Growth and has Inherent Foul Smell. Polymer Coat Over the Subject Molecules are Done for Bacterial Protection (BP) and Smell Masking (SM)

Example 12 Lactic Acid—Polymer Composition is Intended to Prepare Bacterial Protection (BP) and Smell Masking (SM) Over the Subject Molecules PART A: 200 ml water is taken as a vehicle and saturated with 65 gm salt. Furthermore viscosity of vehicle is increased with the aid of viscosity enhancer 1 gm Sodium CMC and water miscible surfactant 1 gms Lecithin are mixed proper to form a uniform blend.

PART B: Subject molecule 50 gm Lactic Acid is slowly added into PART A with constant stirring and the suspension is kept under stirring for 30 minutes with heating temperature at 60° C.

PART C: A catalyst "Cat N" 0.11 gm with DM water is prepared in different container.

Once temperature is gained PART C is poured to above suspension mixture (A+B) with constant stirring.

PART D: Monomer (MAA 7.5 gm, EA 7.5 gm) were used for the synthesis of the polymer. The monomers were mixed in separate container. A catalyst "Cat A" 0.38 gm is mixed with the monomer blend homogeneously.

PART D is poured into uniform dispersion prepared above(A+B+C)

For reaction to initiate and complete the polymerization of monomer over the subject molecule, the mixture is kept at 60-75° C. and pressure 1 kg for time 6 hr. pH of the reaction was maintained at 2.5-3.

And the reaction mixture was purged with the nitrogen gas to provide the inert atmosphere.

The polymer coated Lactic Acid micro particles so synthesized was recovered by filtration and given few washes of water. Once washing is done it is re dispersed in water to make a feed of spray dryer.

(V) Ascorbic Acid and Zinc Sulphate are Moisture Sensitive Molecules. Polymer Coat Over the Subject Molecules are Done for Moisture Protective Film (MF)

Example 13: Ascorbic Acid-Polymer Composition is Intended to Prepare Moisture Protective Film (MF) Over the Subject Molecules PART A: 250 ml Castor oil ethoxylate is taken as a vehicle. And water miscible surfactant 2 gm Tween80 and 0.7 gm SLES are mixed proper to form a uniform blend.

PART B: Subject molecule 50 gm Ascorbic Acid is blended with 10 gm Aerosil R972 it is then slowly added to the PART A with constant stirring and the suspension is kept under stirring for 30 minutes with heating temperature at 60° C.

PART C: A catalyst "Cat N" 0.3 gm with DM water is prepared in different container.

Once temperature is gained PART C is poured to above suspension mixture (A+B) with constant stirring.

PART D: Monomer (MAA 25 gm, MM 25 gm) were used for the synthesis of the polymer. The monomers were mixed in separate container. A catalyst "Cat A" 0.5 gm is mixed with the monomer blend homogeneously.

PART D is poured into uniform dispersion prepared above PARTS (A+B+C)

For reaction to initiate and complete the polymerization of monomer over the subject molecule, the mixture is kept at 80-85° C. and pressure 1 kg for time 6 hr. pH of the reaction was maintained at 2.5-3.

And the reaction mixture was purged with the nitrogen gas to provide the inert atmosphere.

The polymer coated Lactic Acid micro particles so synthesized was recovered by filtration and given few washes of water. Once washing is done it is re dispersed in water to make a feed of spray dryer.

Example 14: Zinc Sulphate-Polymer Composition is Intended to Prepare Moisture Protective Film (MF) Over the Subject Active Substance PART A: 250 ml Soya oil ethoxylate is taken as a vehicle. Water miscible surfactant 0.7 gm SLS and 2 gm Tween80 are mixed proper to form a uniform blend.

PART B: Subject molecule 50 gm Zinc Sulphate is blended with 10 gm Aerosil R972 it is then slowly added into PART A with constant stirring and the suspension is kept under stirring for 30 minutes with heating temperature at 70° C.

PART C: A catalyst "Cat p" 0.4 gm with DM water is prepared in different container.

Once temperature is gained PART C is poured to above suspension mixture (A+B) with constant stirring.

PART D: Monomer (MAA 25 gm, MM 25 gm) were used for the synthesis of the polymer. The monomers were mixed in separate container. A catalyst "Cat A" 0.6 gm is mixed with the monomer blend homogeneously.

PART D is poured into uniform dispersion prepared above PARTS (A+B+C)

For reaction to initiate and complete the polymerization of monomer over the subject molecule, the mixture is kept at temperature 78-83° C. and pressure 2 kgs for time 6 hrs. pH of the reaction was maintained at 6.8-7.5.

And the reaction mixture was purged with the nitrogen gas to provide the inert atmosphere.

The polymer coated Lactic Acid micro particles so synthesized was recovered by filtration and given few washes of water. Once washing is done it is re dispersed in water to make a feed of spray dryer.

(VI) Aluminium Copper and Iron are the Subject Molecules Which are Subject to Oxidation. Polymer Coat Over the Subject Molecules are Done for Oxidation Protactive Film (OF)

Example 15: Aluminium-Polymer Composition is Intended to Prepare Oxidation Protactive Film (OF) Over the Subject Molecules PART A: 200 ml of water is taken as a Vehicle. Furthermore viscosity of vehicle is increase with the aid of Viscosity enhancer 1 gm Sodium CMC. And water miscible surfactant 1 gms Sorbitan Mono Oleate is mixed proper to form a uniform blend.

PART B: Subject Molecule 25 gm Aluminium is slowly added into PART A with constant stirring and the suspension is kept under stirring for 30 minutes.

PART C: The Monomers (MM 9 gm, EA 16 gm) were mixed in separate container for 10 minutes. After that a Catalyst "Cat N" 0.2 gm is mixed to the homogeneously blended monomers.

PART C is poured into uniform dispersion of PARTS (B+A)

For reaction to initiate and complete the drug and monomer mixture is kept at 78-80° C. & Pressure 1 kg for time 6 hr.

pH of the reaction was maintained at 6.5-7.

And the reaction mixture was purged with the nitrogen Gas to provide the inert atmosphere.

The polymer coated over Aluminium micro particles so synthesized was recovered by filtration and given few washes of water. Once washing is done it is redispersed in water to make a feed of spray dryer, and so dried uniform powder is collected out of the spray dryer Example 16: Copper-Polymer Composition is Intended to Prepare Oxidation Protactive Film (OF) Over the Subject Molecules PART A: 200 ml of water is taken as a vehicle. Furthermore viscosity of vehicle is increase with the aid of Viscosity enhancer 1 gm Sodium CMC and water miscible surfactant 1 gm Sorbitan Mono Oleate is mixed proper to form a uniform blend.

PART B: Subject Molecule 26 gm Copper is slowly added into PART A with constant stirring and the suspension is kept under stirring for 30 minutes.

PART C: The Monomers (MM 9 gm, and EA 16 gm) were mixed in separate container for 10 minutes. After that a Catalyst "Cat N" 0.2 gm is mixed to the homogeneously blended monomers.

PART C is poured into uniform dispersion of PART B+A

For reaction to initiate and complete the drug and monomer mixture is kept at temperature 78-80° C. & Pressure 1.5 kg for Time 6 hr.

pH of the reaction was maintained at 6.5-7.

And the reaction mixture was purged with the nitrogen Gas to provide the inert atmosphere.

The polymer coated over Copper micro particles so synthesized was recovered by filtration and given few washes of water. Once washing is done it is redispersed in water to make a feed of spray dryer, and so dried uniform powder is collected out of the spray dryer.

Example 17: Ferrous Powder-Polymer Composition is Intended to Prepare Oxidation Protactive Film (OF) Over the Subject Molecules PART A: 200 ml of water is taken as a vehicle. Furthermore viscosity of vehicle is increase with the aid of Viscosity enhancer 1 gm Sodium CMC and water miscible surfactant 1 gm Sorbitan Mono Stearate is mixed proper to form a uniform blend.

PART B: Subject Molecule 26 gm Copper is slowly added into PART A with constant stirring and the suspension is kept under stirring for 30 minutes.

PART C: The Monomers (MM 9 gm, and EA 16 gm) were mixed in separate container for 10 minutes. After that a Catalyst "Cat N" 0.2 gm is mixed to the homogeneously blended monomers.

PART C is poured into uniform dispersion of PART B+A

For reaction to initiate and complete the drug and monomer mixture is kept at Temperature 78-80° C. & Pressure 1.5 kg for Time 6 hr.

pH of the reaction was maintained at 6.5-7.

And the reaction mixture was purged with the nitrogen Gas to provide the inert atmosphere.

The polymer coated over Copper micro particles so synthesized was recovered by filtration and given few washes of water. Once washing is done it is redispersed in water to make a feed of spray dryer, and so dried uniform powder is collected out of the spray dryer where the drying is carried out at the temperature range of 60 to 200° C. where in drying is carried out without affecting the properties of subject molecules.

With the aim of solving the problems of the prior art through the process devised a pharmaceutical composition of unique characteristics is obtained at each attempt leading to numerous formulations and which deliver the objective as desired.

For the purpose of explanation, the parameters and the substances used, the results obtained by altering the factors as required and responsible for achieving the objectives are made available in tabular form for understanding the essentiality of the invention as disclosed in the examples 1, 2, 3, . . . , 14, 15, 16 and 17. The said tabular form is partitioned to two major parts as follows:

TABLE

PART (1)

| App. | Sr. No. | Subject Molecule | Molecule To Polymer (%) | Polymer Composition Acrylic Monomers | Surfactant | Viscosity Enhancer |
|---|---|---|---|---|---|---|
| TM SR | 1 | Azithromycin Dihydrate | 35% | MM(8.75%) RM-88(8.75%) DMA(17.5) | L1 | SC |
| | 2 | Paracetamol | 50% | MM(12.5%) RM-88(12.5%) DMA(25%) | E2 | SC |
| | 3 | Cephalexin | 50% | MM(17.5%) BA(17.5%) DMA(15%) | S3 T4 | XG |
| | 4 | Chloroquine Phosphate | 50% | MM(17%) BA(15.5) DMA(17.5%) | E2 | SC |
| | 5 | Erythromycin Ethyl Sucsinate | 50% | MA(12.5%) MM(12.5%) DMA(25%) | S3 | GG |
| | 6 | Linezolid | 50% | MM(12.5%) RM-88(12.5%) DMA(25%) | E1 | SC |
| TM CT | 7 | Clarithromysin | 30% | MM(12%) RM-88(12%) DMA(26%) | L1 | SC |
| | 8 | Ampicillin | 50% | MM(15%) RM-88(15%) DMA(20%) | E1 | SC |
| TM EC | 9 | Metronidazole Benzoate | 50% | MA(25%) AA(25%) | E2 | SC |
| | 10 | Ibuprofen | 30% | EA(15%) MAA(15%) | L1 | SC |
| | 11 | Cefadroxil | 50% | MA(31.5)% MM(13.5%) MAA(5%) | S3 T3 | SC |
| TM BP SM | 12 | Lactic Acid | 50% | MM(25%) MAA(25%) | S3 T4 | XG |
| MF | 13 | Ascorbic Acid | 50% | MM(25%) MAA(25%) | S4 T4 | — |
| | 14 | Zinc Sulphate | 50% | MM(25%) MAA(25%) | S3 T4 | — |
| OF | 15 | Aluminum Powder | 50% | MM(18%) EA(32%) | S1 | SC |
| | 16 | Cupper Powder | 50% | MM(18%) EA(32%) | S2 | SC |
| | 17 | Ferrous Powder | 50% | MM(18%) EA(32%) | S1 | SC |

TABLE (PART 2)

| Sr. No. | Catalyst | Temp (° C.) | P (Kg) | T(min) | Add. Salt | Vehicle | Gas | Ph |
|---|---|---|---|---|---|---|---|---|
| 1 | CatA (2.4%) | 55-75 | 2 | 6 Hr | No | Water | N2 | 8.5-9.0 |
| 2 | CatA (3.5%) CatN (2%) | 60-75 | 2 | 5 Hr | Yes | Water | N2 | 7-8 |
| 3 | CatA (3%) CatN (0.5) | 75-80 | 1 | 5 Hr 30 min | Yes | Water | N2 | 3-6 |
| 4 | CatA (3%) | 80-85 | 2 | 5 Hr | Yes | Water | N2 | 4-6.5 |
| 5 | CatA (0.4%) CatP (1%) | 75-80 | 1.5 | 5 Hr 40 min | Yes | Water | N2 | 8.5-9 |
| 6 | CatA (2%) | 70-85 | 2 | 5 Hr | Yes | Water | N2 | 8.5-9 |
| 7 | CatA (4%) | 55-75 | 1 | 6 Hr | No | Water | N2 | 8.5-9 |
| 8 | CatA (4%) CatN (0.2) | 80-85 | 1.5 | 5 Hr | Yes | Water | N2 | 5-7.5 |
| 9 | CatA (0.5%) CatG (0.5%) | 78-80 | 2 | 6 Hr | No | Water | N2 | 5-7 |
| 10 | CatA(0.76%) CatN(0.22%) | 60-75 | 1 | 6 Hr | Yes | Water | N2 | 2.5-3 |
| 11 | CatN (0.8) | 75-80 | 1 | 6 Hr | Yes | Water | N2 | 2.5-3 |
| 12 | CatA (1%) CatN (0.3%) | 75-80 | 1.5 | 5 Hr | Yes | Water | N2 | 4-5 |
| 13 | CatA (0.5%) CatN (0.3%) | 80-85 | 1 | 6 Hr | Yes | Castor Oil Ethoxylate | N2 | 2.5-3 |
| 14 | CatA (0.6%) CatP (0.4%) | 78-83 | 2 | 6 Hr | Yes | Soya Oil Ethoxylate | N2 | 6.8-7.5 |
| 15 | CatN (0.4%) | 78-80 | 1 | 6 Hr | No | Water | N2 | 6.5-7 |
| 16 | CatN (0.4%) | 78-80 | 1.5 | 6 Hr | N | Water | N2 | 6.5-7 |
| 17 | CatN (0.4%) | 78-80 | 1.5 | 6 Hr | N | Water | N2 | 6.5-7 |

The above table and parts thereof discloses the result of the invention with variations and alternatives which are the narrower prospective of the theme of the invention.

As discussed above, the monomers selected are the derivatives of acrylic acid and methacrylic acid. The subject molecule can be organic compounds, inorganic compounds, metal compounds, and Plastics.

The subject molecules are API which is water soluble, water insoluble or partially water soluble. Further, there is provision of adding a rheological modifier to aid the process and the rehology modifier is viscosity enhancing agent.

The pH sensitive polymer covering subject molecule solubilizes or swells in the acidic pH<3 as found in stomach and remains insoluble or de swelled in the pH range>3.5.

The pH sensitive polymer covering subject molecule can be used for pharmaceutical formulations such as solid, semisolid, and liquid dosage forms and the microparticles of drug coated with the polymer are suspend able in liquid for liquid formulations.

The pharmaceutical composition made out of the process is formulated in a solid dosage form selected from tablets, strips, chewable, mouth dissolving, effervescent and dispersible tablets. Further, the pharmaceutical composition is formulated in a liquid dosage form selected from dry syrup and suspension and in liquid dosage form in gel, Ointment, Cream and Paste.

The viscosity enhancer is selected from the group consisting of acacia, carbomer, carboxy methyl cellulose calcium, carboxy methyl cellulose sodium, hydroxy ethyl cellulose hydroxy propyl cellulose, hydroxy propyl methyl cellulose, methylcellulose, polyvinyl pyrroiidone, powdered cellulose, sodium alginate and tragacanth.

The viscosity enhancer is also selected from Surfactant groups of Ionic surfactants, Anionic surfactants, Non ionic surfactants and Amphoteric surfactants.

As any person skilled in the art will readily appreciate, the above description is meant as an illustration of implementation of the principles of this invention. The description is not intended to limit the scope or application of this invention in that the invention is susceptible to modification, variation and change, without departing from the spirit of this invention.

The invention claimed is:

1. A process for preparing a drug-polymer composition, comprising:
   (a) preparing a uniform blend of a vehicle saturated with an edible mineral salt and a surfactant as part A;
   (b) preparing a suspension comprising an amount of active drug subject molecules and a thickener that is added to part A with constant stirring resulting in a suspension as part B;
   (c) preparing a catalyst content comprising a first catalyst and demineralized water as part C;
   (d) adding part C to part B with constant stirring to provide part D;
   (e) separately preparing a homogeneous blend containing one or more monomers, from which a polymer is formed, and a second catalyst and pouring the homogenous blend into part D;
   (f) initiating a reaction in an inert atmosphere to complete polymerization of the one or more monomers in the contents of step (e) by maintaining a pH, temperature, pressure, and time sufficient to complete polymerization of the one or more monomers, thereby providing a pH sensitive polymer coating over the subject molecules;
   (g) recovering a polymerized product from step (f) by filtration and washing repeatedly;
   (h) feeding the contents of step (g) to a spray drier for drying in order to obtain the drug-polymer composition.

2. The process of claim 1, wherein the one or more monomers are derivatives of acrylic acid and methacrylic acid.

3. The process of claim 1, wherein the molecular weight of the polymer ranges from 10,000 to 1,000,000.

4. The process of claim 1, wherein a ratio of the polymer to the subject molecules is in the range of 50:1 to 0.2:1.

5. The process of claim 1, wherein the second catalyst is a redox initiator and the first catalyst is an oxidizing agent.

6. The process of claim 1, wherein the subject molecules are organic compounds, inorganic compounds and/or metal compounds.

7. The process of claim 1, wherein the subject molecules are organic and/or inorganic active pharmaceutical ingredients (APIs).

8. The process of claim 1, wherein the subject molecules comprise an API which is water soluble, water insoluble or partially water soluble.

9. The process of claim 1, wherein a rheology modifier is added to aid the process.

10. The process of claim 9, wherein the rheology modifier is selected from a viscosity enhancing agent and/or wetting agent.

11. The process of claim 10, wherein the viscosity enhancing agent is selected from acacia, carbomer, carboxy methyl cellulose calcium, carboxy methyl cellulose sodium, hydroxy ethyl cellulose hydroxy propyl cellulose, hydroxy propyl methyl cellulose, methylcellulose, polyvinyl pyrrolidone, powdered cellulose, sodium alginate and tragacanth, guar gum, gumacasia, or xenthan gum.

12. The process of claim 1, wherein the drug-polymer composition is used for pharmaceutical formulations selected from solid, semisolid, and liquid dosage forms.

13. The process of claim 1, wherein the polymer-drug composition is formulated in a pharmaceutical solid dosage form selected from a tablet, a capsule, a strip, a chewable tablet, a mouth dissolving tablet, an effervescent tablet, or a dispersible tablet.

14. The process of claim 1, wherein the polymer-drug composition is formulated in a pharmaceutical liquid dosage form selected from a dry syrup or a suspension.

15. The process of claim 1, wherein the polymer-drug composition is formulated in a pharmaceutical semi solid dosage form selected from a gel, an ointment, a cream or a paste.

16. The process of claim 1, wherein the % weight ratio of each of the first catalyst and the second catalyst to the one or more monomers is in the range of 0.1 to 5.

17. The process of 1, wherein the temperature ranges from 20-95° C. and the time ranges from 1-24 hours.

18. The process of claim 1, wherein the polymerization time is 1 to 2 hours.

19. The process of claim 1, wherein the % weight ratio of the vehicle to the monomer during the synthesis of the pH sensitive polymer coating is 10 to 95.

20. The process of claim 1, wherein the pH ranges from 2 to 10.

21. The process of claim 1, wherein the inert atmosphere is nitrogen gas.

22. The process of claim 1, wherein the drying is carried out at the temperature range of 40 to 200° C.

23. The process of claim 1, wherein the subject molecules further comprise a plastic material.

* * * * *